United States Patent

Pugin

[11] Patent Number: 6,015,919
[45] Date of Patent: Jan. 18, 2000

[54] DIHALOGENATED FERROCENES AND PROCESSES FOR THE PREPARATION THEREOF

[75] Inventor: Benoît Pugin, Münchenstein, Switzerland

[73] Assignee: Novartis AG, Basel, Switzerland

[21] Appl. No.: 09/246,203

[22] Filed: Feb. 8, 1999

Related U.S. Application Data

[62] Division of application No. 08/930,171, Oct. 9, 1997, Pat. No. 5,925,778.

[30] Foreign Application Priority Data

Apr. 11, 1995 [CH] Switzerland .............. 1067/95

[51] Int. Cl.$^7$ .............. C07F 17/02; C07B 31/00
[52] U.S. Cl. .............. 556/145; 556/143; 556/144; 502/152; 502/154
[58] Field of Search .............. 556/14, 11, 13, 556/143, 144, 145

[56] References Cited

U.S. PATENT DOCUMENTS 5,244,857  9/1993  Pugin et al. .............. 502/167
5,252,751  10/1993  Pugin et al. .............. 549/214

(List continued on next page.)

FOREIGN PATENT DOCUMENTS 9632400  10/1996  WIPO .
9702232  1/1997   WIPO .

OTHER PUBLICATIONS

Achiwa, K., "Catalytic Asymmetric Hydrogenations with Polymer Supported Chiral Pyrrolidinephosphine–Rhodium Complexes," Chemistry Letters, 1978, pp. 905–908.

(List continued on next page.)

*Primary Examiner*—Mukund J. Shah
*Assistant Examiner*—Pavanaram K Sripada
*Attorney, Agent, or Firm*—Stephen G. Kalinchak; Gabriel Lopez

[57] ABSTRACT

The invention relates to a compound of formula I

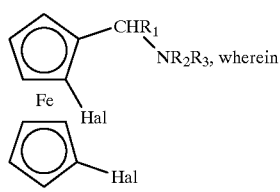

(I)

$R_1$ is $C_1$–$C_8$alkyl, phenyl or phenyl substituted by from 1 to 3 $C_1$–$C_4$alkyl or $C_1$–$C_4$alkoxy substituents;

$R_2$ and $R_3$ are each independently of the other hydrogen or $C_1$–$C_{12}$alkyl; and Hal is F, Cl, Br or I.

Compounds of formula I are valuable intermediates for compounds of formula III which are also a subject of this invention:

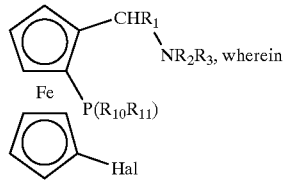

(III)

$R_1$, $R_2$, $R_3$ and Hal are as defined above;

$R_{10}$ and $R_{11}$ are identical or different and are $C_1$–$C_{12}$alkyl, $C_5$–$C_{12}$cycloalkyl, phenyl, $C_5$–$C_{12}$cycloalkyl substituted by $C_1$–$C_4$alkyl or by $C_1$–$C_4$alkoxy, or phenyl substituted by from one to three $C_1$–$C_4$alkyl, $C_1$–$C_4$alkoxy, —$SiR_4R_5R_6$, halogen, —$SO_3M$, —$CO_2M$, —$PO_3M$, —$NR_7R_8$, —[$^+NR_7R_8R_9$]$X^-$ or $C_1$–$C_5$fluoroalkyl substituents; or the group —$PR_{10}R_{11}$ is a radical of formula IV, IVa, IVb or IVc

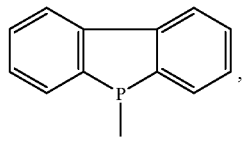

(IV)

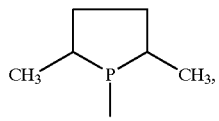

(IVa)

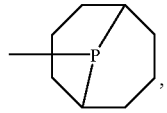

(IVb)

(IVc)

$R_4$, $R_5$ and $R_6$ are each independently of the others $C_1$–$C_{12}$alkyl or phenyl;

$R_7$ and $R_8$ are H, $C_1$–$C_{12}$alkyl or phenyl or $R_7$ and $R_8$ together are tetramethylene, pentamethylene or 3-oxa-1,5-pentylene;

$R_9$ is H or $C_1$–$C_4$alkyl;

M is H or an alkali metal;

$X^-$ is the anion of a monobasic acid.

19 Claims, No Drawings

U.S. PATENT DOCUMENTS

| | | | |
|---|---|---|---|
| 5,371,256 | 12/1994 | Togni et al. | 556/14 |
| 5,466,844 | 11/1995 | Spindler et al. | 556/11 |
| 5,583,241 | 12/1996 | Spindler | 556/143 |
| 5,627,293 | 5/1997 | Pugin | 556/11 |
| 5,783,715 | 7/1998 | Pugin | 556/11 |
| 5,925,778 | 7/1999 | Pugin | 556/144 |

OTHER PUBLICATIONS

Cullen et al., "Polymer Supported Ferrocene Derivatives. Catalytic Hydrosilylation of Olefins by Supported Palladium and Platinum Complexes," J. of Organom. Chem., vol. 333, 1987, pp. 269–280.

Kim et al., "Functionalized Organometallic Ligand (1) Synthesis of Some Ferrocene Derivatives of Cyclohexyl–and Cyclopentadienyl–phosphines," Bull. Korean Chem. Soc., vol. 13, No. 6, 1992, pp. 588–592.

Kovar et al., "A Convenient Route to 1'1'–Dihalogenated Ferrocenes", Organometallics in Chemical Synthesis, vol. 1 1970/1971, pp. 173–181.

Togni, A., "Developing New Chiral Ferrocenyl Ligands for Asymmetric Catalysis: A Personal Account," Chimia, vol. 50, 1996, pp. 86–93.

DIHALOGENATED FERROCENES AND PROCESSES FOR THE PREPARATION THEREOF

This application is a divisional of U.S. application Ser. No. 08/930,171, filed Oct. 9, 1997 now U.S. Pat. No. 5,925,778. The entire contents of the '171 application are incorporated herein by reference.

The invention relates to ferrocenes substituted in the 1,2- and 1'-positions and to processes for the preparation thereof.

Ferrocenyldiphosphine ligands having a silylene group are important intermediates for ferrocenyldiphosphines, and their metal complexes with transition metals such as rhodium or iridium, bonded via that silylene group to inorganic or polymeric organic carriers. Those complexes are used widely in the hydrogenation of organic double or triple bonds, especially olefinic double bonds and carbon-hetero atom double bonds. The complexes are suitable especially for enantioselective hydrogenation using chiral ferrocenyldiphosphines and corresponding prochiral unsaturated compounds.

EP-A-0-496 699 and EP-A-0 496 700 disclose silane-group-containing dioxolan- and pyrrolidine-diphosphines and their rhodium or iridium complexes that are fixed to an inorganic carrier such as, for example, a silicate. In that manner there is obtained in the hydrogenation a heterogeneous reaction mixture from which the inorganically fixed catalyst can readily be separated when the reaction is complete.

W. R. Cullen et. al. describe in J. of Organometallic Chemistry, 333 (1987), 269–280 ferrocene derivatives, such as, for example, N,N-dimethyl-1-(2-diphenylphosphino-ferrocenyl)ethylamine that is bonded directly to an oxidised polystyrene group. In the procedure proposed therein a maximum of 20% of the ferrocene derivative used is bonded to the polymeric carrier and the ferrocenyl ligand is bonded to the polymer non-specifically and non-selectively partly via one or the other cyclopentadienyl ring. As a result of the direct bonding to the polymer skeleton the mobility of the phosphine ligand is likewise restricted.

It appears desirable to start from starting materials having known properties and to modifiy those starting materials using catalytically active compounds in such a manner that the properties are altered only very slightly and there are no inclusions or any other alterations to the catalytically active part; depending on the hydrogenation reaction, either inorganically or organically bonded ferrocenyldiphosphine ligands may be more advantageous.

However, it is also possible further to functionalise those silylated ferrocenyldiphosphines in such a manner that they are copolymerisable, for example, via an olefinically unsaturated bond. Such procedures are described, for example, in J. Org. Chem. 1981, 46, 2960–2965.

In the case of polymer-bonded ferrocenyldiphosphine ligands, for example, the reaction to be catalysed can be carried out heterogeneously or homogeneously depending upon the polymer chosen. The polymer may be so selected and also subsequently so modified in a targeted manner that the catalyst can readily be separated off and re-used after the reaction. The catalysts may be re-used several times. By the choice of the polymer it is possible to match the catalyst in an optimum manner to the reaction medium during the hydrogenation step and then to remove it completely afterwards, which is of particular importance in relation to hydrogenation carried out on an industrial scale.

In all cases the recovery of the noble metals present is facilitated if the catalyst has to be changed after frequent recycling. It is often also possible to dispense with further purification of the hydrogenated product since the catalyst can generally be removed quantitatively.

Ferrocenyldiphosphines that contain an organic radical bonded via a silylene group to a cyclopentadienyl ring can be immobilised in a simple manner both on inorganic and on polymeric organic carriers or, after the introduction of a polymerisable group, can be immobilised also by copolymerisation. With rhodium and iridium the immobilised ferrocenyldiphosphine ligands form complexes that can be used as highly active catalysts in the enantioselective hydrogenation of carbon-carbon, carbon-nitrogen or carbon-oxygen double bonds. The selectivity and the total yield are surprisingly high for immobilised systems. The iridium catalysts are especially well suited to imine hydrogenation since they have clearly the highest activity and the highest catalyst productivity in comparison with other immobilised systems. Their selectivity is likewise very good. The catalysts can readily be separated from the reaction solution and used again. There are virtually no losses of metal and ligand. The use of those immobilised catalysts therefore enables hydrogenation to be carried out economically, especially on an industrial scale.

The preparation of such immobilised ferrocenyldiphosphines has been made possible only by the provision of correspondingly functionalised ferrocenyldiphosphines. Those intermediates and the preparation thereof are therefore of great importance.

Ferrocenes that are substituted by two phosphine groups at a cyclopentadienyl ring are known, and their preparation and use as ligands in metal complexes for stereoselective hydrogenation is described, for example, in EP-A-564 406.

No process has been disclosed hitherto that allows, for example stereoselectively in (R)- or (S)-N,N-dimethyl-1-ferrocenylethylamine, in a first step the introduction of a phosphorus group as an electrophile with high selectivity at an already substituted cyclopentadienyl ring and in a second step the introduction of a silylene group selectively at the other cyclopentadienyl ring. Using that procedure, however, it is possible for the first time to prepare a number of valuable intermediates for ferrocenyldiphosphines and their metal complexes.

Dihalogenated, but otherwise unsubstituted, ferrocenes having a halogen atom bonded to both cyclopentadienyl groups in the 1- and 1'-positions are known, for example, from R. F. Kovar et al., Organometal. Chem. Syn., 1 (1970/1971) 173–181. Their preparation by means of lithiation and subsequent halogenation is likewise diclosed therein.

However, 1,1'-dihalogenated ferrocenes substituted in the 2-position have not been disclosed hitherto.

The invention accordingly relates to compounds of formula I

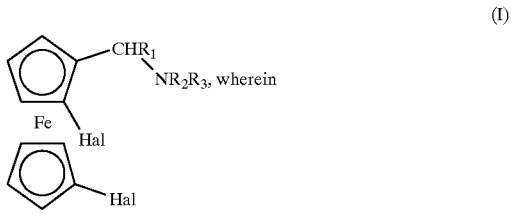

$R_1$ is $C_1$–$C_8$alkyl, phenyl or phenyl substituted by from 1 to 3 $C_1$–$C_4$alkyl or $C_1$–$C_4$alkoxy substituents;

$R_2$ and $R_3$ are each independently of the other hydrogen or $C_1$–$C_{12}$alkyl; and Hal is F, Cl, Br or 1.

$R_1$ as alkyl is preferably linear. It preferably contains from 1 to 4 carbon atoms. Examples of such alkyl are methyl, ethyl, n- and iso-propyl, n-, iso- and tert-butyl, pentyl, hexyl, heptyl and octyl. Preference is given to methyl and ethyl, and methyl is especially preferred.

$R_1$ as substituted phenyl preferably contains 1 or 2 substituents. Alkyl substituents may be, for example, methyl, ethyl, n- and iso-propyl, n-, iso- and tert-butyl; methyl and ethyl are preferred. Alkoxy substituents may be, for example, methoxy, ethoxy, n- and iso-propoxy, n-iso- and tert-butoxy; methoxy and ethoxy are preferred. In a group of compounds of formula I, $R_1$ is preferably phenyl or phenyl substituted by 1 or 2 $C_1$–$C_4$alkyl or $C_1$–$C_4$alkoxy substituents.

$R_2$ and $R_3$ as alkyl may be linear or branched. Examples of $C_1$- to $C_8$-alkyl are mentioned above and include in addition the various isomers of nonyl, decyl, undecyl and dodecyl. $R_2$ and $R_3$ may also be bonded to one another and form a cyclic alkyl group. Resulting examples are pyrrolidine and piperidine.

Preferably $R_2$ and $R_3$ are each independently of the other hydrogen, methyl or ethyl, and are especially both hydrogen or methyl.

Hal is preferably Cl, Br or I.

The compounds of formula I can be prepared in accordance with analogous processes in a manner known per se, as described, for example, by R. F. Kovar et al., Organometal. Chem. Syn., 1 (1970/1971) 173–181 for the reaction of di-lithiated compounds with halogenating agents or by T. Hayashi et al., Bull Chem. Soc. Jpn., 53 (1980) 1138–1151 for stereo-selective lithiation.

The invention relates also to a process for the preparation of compounds of formula I wherein a compound of formula II

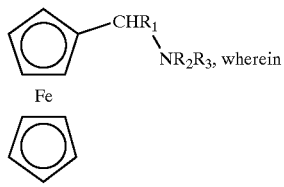

(II)

$R_1$, $R_2$ and $R_3$ are as defined above, is reacted in an inert organic solvent first with an equivalent of alkyllithium and then, in the presence of an amine complexing agent for Li, with a second equivalent of alkyllithium and the product is then reacted with a halogenating agent.

An example of an amine complexing agent for Li is N,N,N,N-tetramethylethylenediamine. Alkyllithium is to be understood in the context of this invention as being preferably tert-butyl-, sec-butyl- or n-butyl-lithium.

Halogenating agents are known in the general prior art for many reactions. Some are also mentioned, for example, in Gmelin, Handbuch der Anorganischen Chemie, Eisen-Organische Verbindungen Teil A Ferrocen 7, Eighth Edition, Springer Verlag 1980, pages 128–136.

Preference is given to a halogenating agent selected from the group consisting of $Cl_2$, hexa-chloroethane, 1,2-dichlorotetrafluoroethane, toluene-4-sulfonyl chloride, $Br_2$, 1,2-dibromo-tetrachloroethane, 1,2-dibromotetrafluoroethane, toluene-4-sulfonyl bromide, 2,3-dimethyl-2,3-dibromobutane, $I_2$, 1,2-diiodotetrafluoroethane, perfluoropropyl iodide, perfluoroethyl iodide, toluene-4-sulfonyl iodide and perfluoromethyl iodide.

The compounds of formula I act as starting materials for the preparation of compounds of formula III which are likewise novel and a subject of this invention.

The invention relates also to compounds of formula III

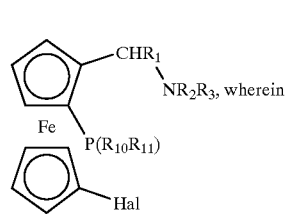

(III)

$R_1$, $R_2$, $R_3$ and Hal are as defined above, $R_{10}$ and $R_{11}$ are identical or different and are $C_1$–$C_{12}$alkyl, $C_5$–$C_{12}$cycloalkyl, phenyl, $C_5$–$C_{12}$cycloalkyl substituted by $C_1$–$C_4$alkyl or by $C_1$–$C_4$alkoxy, or phenyl substituted by from one to three $C_1$–$C_4$alkyl, $C_1$–$C_4$alkoxy, —$SiR_4R_5R_6$, halogen, —$SO_3M$, —$CO_2M$, —$PO_3M$, —$NR_7R_8$, —$[^+NR_7R_8R_9]X^-$ or $C_1$–$C_5$fluoroalkyl substituents; or the group —$PR_{10}R_{11}$ is a radical of formula IV, IVa, IVb or IVc

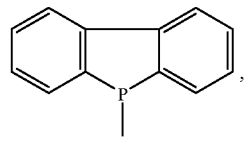

(IV)

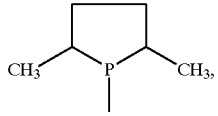

(IVa)

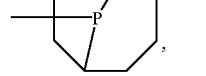

(IVb)

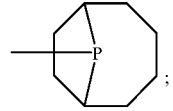

(IVc)

$R_4$, $R_5$ and $R_6$ are each independently of the others $C_1$–$C_{12}$alkyl or phenyl;

$R_7$ and $R_8$ are H, $C_1$–$C_{12}$alkyl or phenyl or $R_7$ and $R_8$ together are tetramethylene, pentamethylene or 3-oxa-1,5-pentylene;

$R_9$ is H or $C_1$–$C_4$alkyl;

M is H or an alkali metal;

$X^-$ is the anion of a monobasic acid.

$R_{10}$ and $R_{11}$ as alkyl may be linear or branched and they contain preferably from 1 to 8 and especially from 1 to 4 carbon atoms. Examples of such alkyl are methyl, ethyl, n- and iso-propyl, n-, iso- and tert-butyl, pentyl, hexyl, heptyl, octyl, nonyl, decyl, undecyl and dodecyl. Methyl, ethyl, n- and iso-propyl, n-, iso- and tert-butyl are preferred. When $R_{10}$ and $R_{11}$ are identical, as alkyl they are especially isopropyl or tert-butyl.

$R_{10}$ and $R_{11}$ as cycloalkyl contain preferably from 5 to 8 and especially 5 or 6 ring carbon atoms. Examples of cycloalkyl are cyclopentyl, cyclohexyl, cycloheptyl, cyclooctyl, cyclodecyl and cyclododecyl. Preference is given to cyclopentyl and cyclohexyl, and cyclohexyl is especially preferred.

The cycloalkyl may be substituted, for example by from 1 to 3 alkyl or alkoxy substituents. Examples of such substituents have been given above. Methyl and ethyl and methoxy and ethoxy are preferred. Examples of substituted cycloalkyl are methyl- and methoxy-cyclopentyl and -cyclohexyl.

$R_{10}$ and $R_{11}$ as substituted phenyl preferably contain 1 or 2 substituents. When phenyl contains 2 or 3 substituents, those substituents may be identical or different.

Examples of alkyl and alkoxy substituents have been given above; preferred alkyl and alkoxy substituents for phenyl are methyl, ethyl and methoxy and ethoxy.

When the phenyl substituent is halogen, it is preferably —F, —Cl or —Br.

When the phenyl substituent is $C_1$–$C_5$fluoroalkyl, it is fully or partially fluorinated $C_1$–$C_5$alkyl. Examples thereof are the position isomers of mono- to deca-fluoropentyl, mono- to octa-fluorobutyl, mono- to hexa-fluoropropyl, mono- to tetra-fluoroethyl and mono- and di-fluoromethyl. Of the partially fluorinated alkyl radicals, those of the formulae —$CF_2H$ and —$CF_2(C_1$–$C_4$alkyl) are especially preferred. Special preference is given to perfluorinated alkyl. Examples thereof are perfluoropentyl, perfluorobutyl, perfluoropropyl, perfluoroethyl and especially trifluoromethyl. The fluorine-substituted alkyl groups are preferably bonded in the 3-, 4- and 5-positions.

$R_4$, $R_5$ and $R_6$ may be linear or branched alkyl that contains preferably from 1 to 8 and especially from 1 to 4 carbon atoms. Examples of alkyl have been given above. Preferred alkyl is methyl, ethyl, n-propyl, n-butyl or tert-butyl. The substituent —$SiR_4R_5R_6$ is preferably trimethylsilyl.

Of the acid phenyl substituents —$SO_3M$, —$CO_2M$ and —$PO_3M$, the groups —$SO_3M$ and —$CO_2M$ are preferred. M is preferably H, Li, Na or K.

$R_7$ and $R_8$ as alkyl contain preferably from 1 to 6 and especially from 1 to 4 carbon atoms. The alkyl is preferably linear. Preferred examples are methyl, ethyl, n-propyl and n-butyl. $R_9$ as alkyl is preferably methyl.

$X^-$ as an anion of a monobasic acid is preferably $Cl^-$, $Br^-$ or the anion of a carboxylic acid, for example formate, acetate, trichloroacetate or trifluoroacetate.

Preferred examples of $R_{10}$ and $R_{11}$ as substituted phenyl are 2-methyl-, 3-methyl-, 4-methyl, 2- or 4-ethyl-, 2- or 4-isopropyl-, 2- or 4-tert-butyl-, 2-methoxy-, 3-methoxy-, 4-methoxy-, 2- or 4-ethoxy-, 4-trimethylsilyl-, 2- or 4-fluoro-, 2,4-difluoro-, 2- or 4-chloro-, 2,4-dichloro-, 2,4-dimethyl-, 3,5-dimethyl-, 2-methoxy-4-methyl-, 3,5-dimethyl-4-methoxy-, 3,5-dimethyl-4-(dimethylamino)-, 2- or 4-amino-, 2- or 4-methylamino-, 2- or 4-(dimethylamino)-, 2- or 4-$SO_3H$—, 2- or 4-$SO_3Na$—, 2- or 4-[$^+NH_3Cl^-$]—, 3,4,5-trimethylphen-1-yl, 2,4,6-trimethylphen-1-yl, 4-trifluoromethyl-phenyl or 3,5-di(trifluoromethyl)phenyl.

$R_{10}$ and $R_{11}$ are especially preferably cyclohexyl, tert-butyl, phenyl, 2- or 4-methylphen-1-yl, 2- or 4-methoxyphen-1-yl, 2- or 4-(dimethylamino)phen-1-yl, 3,5-dimethyl-4-(dimethylamino)-phen-1-yl or 3,5-dimethyl-4-methoxyphen-1-yl, but especially cyclohexyl, phenyl, 4-methylphen-1-yl or tert-butyl.

The process for the preparation of compounds of formula III is likewise novel and a subject of this invention.

The process for the preparation of compounds of formula III is as follows: in a first step alkyllithium is added to a compound of formula I in an inert organic solvent and allowed to react and then an organic solution of a compound of formula V $ClP(R_{10}R_{11})$ (V) is added and reacted further to form a compound of formula III wherein $R_{10}$ and $R_{11}$ have the definitions and preferred meanings given above.

The substitution of the halogen atom takes place predominantly at the cyclopentadienyl ring that carries the second substituent (alkylamine). It is therefore possible using this process to obtain asymmetric ferrocenes in a good yield, which is of great significance with regard to commercial production.

The process is preferably carried out by adding alkyllithium at a temperature of from −90 to +20° C.

In the second step, the compound of formula V is added preferably at a temperature of from −90 to +20° C.

The invention relates also to ferrocenyldiphosphines of formula VI that are obtained using compounds of formula III as starting materials,

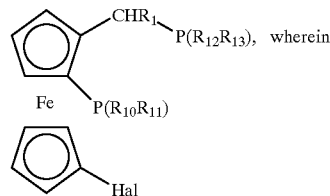

(VI)

$R_1$, $R_{10}$, $R_{11}$ and Hal have the definitions and preferred meanings given above, and $R_{12}$ and $R_{13}$ are each independently of the other $C_1$–$C_{12}$alkyl, $C_5$–$C_{12}$cycloalkyl, phenyl, $C_5$–$C_{12}$cyclo-alkyl substituted by $C_1$–$C_4$alkyl or by $C_1$–$C_4$alkoxy, or phenyl mono- or poly-substituted by from one to three $C_1$–$C_4$alkyl, $C_1$–$C_4$alkoxy, —$SiR_4R_5R_6$, halogen, —$SO_3M$, —$CO_2M$, —$PO_3M$, —$NR_7R_8$, —[$^+NR_7R_8R_9$]$X^-$ or $C_1$–$C_5$fluoroalkyl substituents; or the group —$PR_{12}R_{13}$ is a radical of formula IV, IVa, IVb or IVc (IV)

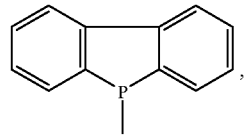

(IVa)

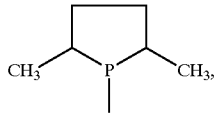

(IVb)

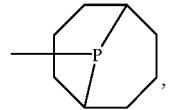

(IVc)

$R_4$, $R_5$, $R_6$, $R_7$, $R_8$, $R_9$, M and $X^-$ have the definitions and preferred meanings given above.

Examples of alkyl, cycloalkyl, substituted phenyl and fluoroalkyl have already been given above and apply also to the definitions of $R_{12}$ and $R_{13}$.

$R_{12}$ and $R_{13}$ are preferably $C_1$–$C_8$alkyl. Examples of $C_1$–$C_8$alkyl have already been mentioned.

$R_{12}$ and $R_{13}$ preferably are identical and are isopropyl or tert-butyl.

$R_{12}$ and $R_{13}$ as cycloalkyl preferably contain from 5 to 8 carbon atoms.

Another preferred group of compounds is obtained when $R_{12}$ and $R_{13}$ are unsubstituted phenyl or phenyl substituted by 1 or 2 substituents.

$R_{12}$ and $R_{13}$ as substituted phenyl are especially preferably 2-methyl-, 3-methyl-, 4-methyl-, 2- or 4-ethyl-, 2- or 4-isopropyl-, 2- or 4-tert-butyl-, 2-methoxy-, 3-methoxy-, 4-methoxy-, 2- or 4-ethoxy-, 4-trimethylsilyl-, 2- or 4-fluoro-, 2,4-difluoro-, 2- or 4-chloro-, 2,4-dichloro-, 2,4-dimethyl-, 3,5-dimethyl-, 2-methoxy-4-methyl-, 3,5-dimethyl-4-methoxy-, 3,5-dimethyl-4-(dimethylamino)-, 2- or 4-amino-, 2- or 4-methylamino-, 2- or 4-(dimethylamino)-, 2- or 4-$SO_3H$—, 2- or 4-$SO_3Na$—, 2- or 4-[$^+NH_3Cl^-$]-, 3,4,5-trimethylphen-1-yl, 2,4,6-trimethylphen-1-yl, 4-trifluoromethyl-phenyl or 3,5-di(trifluoromethyl)phenyl.

A further group of especially preferred compounds is obtained when $R_{12}$ and $R_{13}$ are identical and are phenyl, cyclohexyl, 2- or 4-methylphen-1-yl, 2- or 4-methoxyphen-1-yl, 2- or 4-(dimethylamino)phen-1-yl, 3,5-dimethyl-4-(dimethylamino)phen-1-yl or 3,5-dimethyl-4-methoxyphen-1-yl; $R_{12}$ and $R_{13}$ are more especially identical radicals and are cyclohexyl or phenyl.

Compounds wherein $R_1$ is methyl, $R_{12}$ and $R_{13}$ are each cyclohexyl or phenyl and $R_{10}$ and $R_{11}$ are phenyl, cyclohexyl or tert-butyl are especially preferred.

The process for the preparation of compounds of formula VI can be carried out analogously to processes known in the prior art. For example, that substitution is disclosed in EP-A-612 758.

The process for the preparation of compounds of formula VI comprises reacting a compound of formula III with a compound of formula H—$P(R_{12}R_{13})$ in acetic acid, with $R_{12}$ and $R_{13}$ having the definitions and preferred meanings given above.

The compounds of formulae I, III and VI may be obtained in the form of racemates, pure enantiomers or mixtures of enantiomers. If the synthesis is carried out using enantiomerically pure compounds of formula II as starting materials, there is formed very preferentially only one of the two possible diastereoisomers of the compounds of formula I and consequently also of the compounds of formula III and VI.

If racemates or optically active mixtures are used as starting materials, they can be separated into the stereoisomers by means of known methods, with chromatographic methods generally being preferred. The optical isomers of compounds of formula VI especially are valuable starting materials for the preparation of immobilised hydrogenation catalysts.

The isolation and purification of the compounds is carried out in accordance with methods known per se, for example distillation, extraction, crystallisation and/or chromatographic methods.

The compounds of formula VI can in a first step be lithiated with alkyllithium in known manner, as described, for example, in J. Chem. Soc. Chem. Commun., 1994, 2347–2348. In a further step, a compound of formula VII ClSi($R_{14}$)$_2$—($R_{15}$)—Cl (VII) is then added and reacted to form compounds of formula VIII,

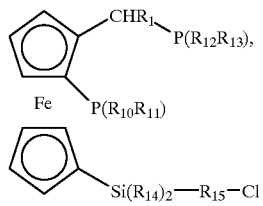

wherein the radicals $R_{14}$ are each independently of the other $C_1$–$C_{12}$alkyl, $C_3$–$C_7$cycloalkyl, benzyl or phenyl or are together $C_4$–$C_{12}$alkylene and $R_{15}$ is $C_1$–$C_{12}$alkylene or phenylene. Preferably $R_{14}$ is methyl and $R_{15}$ is propyl. $R_1$ to $R_{13}$ have been defined above.

The compounds of formula VIII can also be obtained by in a first step lithiating compounds of formula III in accordance with known procedures and then in a second step reacting with compounds of formula VII to form compounds of formula IX

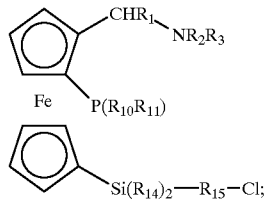

the definitions and preferred meanings of the radicals $R_1$ to $R_{15}$ have been given above.

The compounds of formula IX can be reacted further with a compound of formula H—$P(R_{12}R_{13})$ in acetic acid analogously to procedures known in the prior art and, in this way too, compounds of formula VIII are obtained. That substitution is disclosed by analogy in EP-A-612 758.

Compounds of formula IX may also be used as hydrogenation and hydrosilylation catalysts analogously to the amine-group-containing diphosphines described by Cullen et al. in Can. J. Chem. Vol. 60, 1982, pages 1793 to 1799.

The compounds of formula IX can likewise be immobilised on polymers and used as immobilised ligands in enantioselective catalytic reactions.

The compounds of formula VIII can be reacted further, in accordance with known procedures, with compounds of formula X $NH_2(C_1$–$C_{12}$alkyl) (X) to form compounds of formula VIIIa

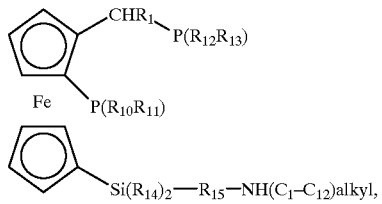

or the compounds of formula VIII are reacted first with potassium phthalimide and then with hydrazine to form compounds of formula VIIIb

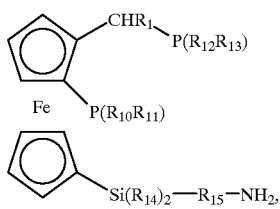

and, optionally, in a further step compounds of formula VIIIa or VIIIb can be reacted with compounds of formula XI $R_a(R_{17}O)_2Si-R_{16}-NCO$ (XI) to form compounds of formula VIIIc

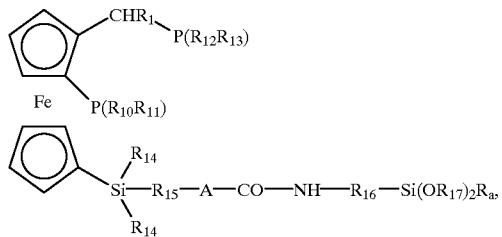

wherein $R_a$ is $C_1-C_4$alkyl or $OR_{17}$, A is NH or $N(C_1-C_{12}$alkyl), $R_{16}$ is $C_1-C_{12}$alkylene and $R_{17}$ is $C_1-C_{12}$alkyl.

The remaining radicals $R_1$ to $R_{15}$ have the definitions given above, including the preferred meanings.

The reaction steps are analogy processes that are described, for example, in EP-A-612 758 and in EP-A496 699. The step of amination to form the compounds of formula VIIIa is known to the person skilled in the art from current reference books on organic chemistry.

The compounds VIIIa and VIIIb can then be reacted to form a polymeric organic material having structural repeating units of formula XII

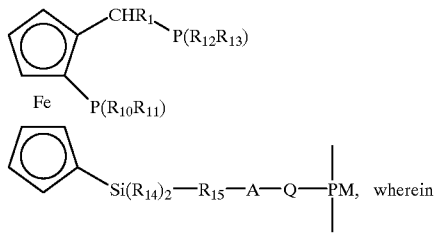

A and $R_1$ to $R_{15}$ are as defined above, Q is a bridge group formed by a diisocyanate, and PM is the radical of a polymer-forming monomer that contains as functional group, bonded directly or in a side chain, a hydroxy group or a primary or secondary amine group which is bonded to the diphosphine via a bridge group Q formed by a diisocyanate.

Preferred diisocyanates are 1,6-bis[isocyanato]hexane, 5-isocyanato-3-(isocyanatomethyl)-1,1,3-trimethylcyclohexane, 1,3-bis[5-isocyanato-1,3,3-trimethyl-phenyl]-2,4-dioxo-1,3-diazetidine, 3,6-bis[9-isocyanato-nonyl]-4,5-di(1-heptenyl)cyclohexene, bis[4-isocyanato-cyclohexyl]methane, trans-1,4-bis[isocyanato]cyclohexane, 1,3-bis[isocyanatomethyl]-benzene, 1,3-bis[1-isocyanato-1-methyl-ethyl]benzene, 1,4-bis[2-isocyanato-ethyl] cyclohexane, 1,3-bis[isocyanatomethyl]cyclohexane, 1,4-bis[1-isocyanato-1-methylethyl]-benzene, bis[isocyanato] isododecylbenzene,1,4-bis[isocyanato]benzene, 2,4-bis [isocyanato]toluene, 2,6-bis[isocyanato]toluene, 2,4-/2,6-bis[isocyanato]toluene, 2-ethyl-1,2,3-tris[3-isocyanato-4-methyl-anilinocarbonyloxy]propane, N,N'-bis[3-isocyanato-4-methyl-phenyl]urea, 1,4-bis[3-isocyanato-4-methylphenyl]-2,4-dioxo-1,3-diazetidine, 1,3,5-tris[3-isocyanato-4-methylphenyl]-2,4,6-trioxohexahydro-1,3,5-triazine, 1,3-bis[3-isocyanato-4-methylphenyl]-2,4,5-trioxoimidazolidine, bis[2-isocyanatophenyl]methane, (2-isocyanatophenyl)-(4-isocyanato-phenyl)-methane, bis [4-isocyanato-phenyl]methane, 2,4-bis[4-isocyanatobenzyl]-1-isocyanatobenzene, [4-isocyanato-3-(4-isocyanato-benzyl)-phenyl]-[2-isocyanato-5-(4-isocyanato-benzyl)-phenyl]methane, tris[4-isocyanato-phenyl]methane, 1,5-bis[isocyanato]naphthalene and 4,4'-bis[isocyanato]-3,3'-dimethyl-biphenyl.

Especially preferred diisocyanates are 1,6-bis[isocyanato] hexane, 5-isocyanato-3-(isocyanatomethyl)-1,1,3-trimethylcyclohexane, 2,4-bis[isocyanato]toluene, 2,6-bis [isocyanato]-toluene, 2,4-/2,6-bis[isocyanato]toluene and bis[4-isocyanato-phenyl]methane.

The polymers according to the invention may be uncrosslinked thermoplastic, crosslinked or structurally crosslinked polymers.

The polymers can be either polymerisates of olefinically unsaturated monomers, for example polyolefins, polyacrylates, polyisoprenes, polybutadiene, polystyrene, polyphenylene, polyvinyl chloride, polyvinylidene chloride or polyallyl compounds. They may also be polyaddition compounds, for example polyurethanes or polyethers. Polycondensed products which may be mentioned are polyesters or polyamides Preference is given to polymer-forming monomers selected from the group consisting of styrene, p-methylstyrene and α-methylstyrene, at least one of which contains a hydroxy group or a primary or secondary amine group bonded as functional group.

Another preferred group of polymers is formed by monomers derived from α,β-unsaturated acids and their esters and amides, the structural units of which contain a hydroxy group or a primary or secondary amine group bonded as functional group.

Special preference is given to the monomers from the group of the acrylates and the $C_1-C_4$alkyl esters thereof, methacrylates and the $C_1-C_4$alkyl esters thereof, acrylamide and acrylonitrile, the structural units of which contain a hydroxy group or a primary or secondary amine group bonded as functional group in the ester or amide group.

Preferably, the hydroxy-functional or primary or secondary amine-functional monomers form from 1 to 100 mole %, preferably from 5 to 100 mole % and especially from 10 to 100 mole %, of the polymer structure in the case of soluble or swellable polymers in which the functional group is already present.

In the case of crosslinked polymers, that are functionalised subsequently, preferably from 1 to 50 mole %, especially from 1 to 20 mole %, hydroxy-functional or primary or secondary amine-functional groups are present, the molar percentages being based on the monomer forming the majority of the polymer.

The loading of the polymer with ferrocenyldiphosphines according to the invention is preferably from 5 to 100 mole %, especially from 5 to 50 mole %, based on the available hydroxy group or primary or secondary amine group of the polymer.

The polymeric carriers can be prepared as follows: polymers having structural repeating units of at least one monomer that contains a hydroxy group or a primary or secondary amine group bonded as functional group directly in the polymer spine or in a side chain A) in a first step are fully or partially reacted, in an inert organic solvent, with a diisocyanate that forms a bridge group Q and in a second step the product is reacted with a diphosphine that contains tertiary phosphine groups bonded in the 1,2-positions of one cyclopentadienyl ring, one of which tertiary phosphine groups is bonded directly and the other of which is bonded via a group $CHR_1$ to the cyclopentadienyl ring, and that contains a silylene group —$Si(R_{14})_2$—$R_{15}$-A- bonded to the other cyclopentadienyl radical; or B) in a first step a diphosphine that contains tertiary phosphine groups bonded in the 1,2-positions of one cyclopentadienyl ring, one of which tertiary phosphine groups is bonded directly and the other of which is bonded via a group $CHR_1$ to the cyclopentadienyl ring, and that contains a silylene group —$Si(R_{14})_2$-$R_{15}$-A- bonded to the other cyclopentadienyl ring is fully or partially reacted, in an inert organic solvent, with a diisocyanate that forms a bridge group Q and in a second step the product is fully or partially reacted with a polymer having structural repeating units of at least one monomer that contains a hydroxy group or a primary or secondary amine group bonded as functional group, and C) any free isocyanate groups that remain are crosslinked with a $C_2$–$C_{24}$diol or $C_2$–$C_{24}$di-amine or removed by reaction with a $C_2$–$C_{12}$alcohol or $C_2$–$C_{12}$amine.

The diisocyanates forming a bridge group Q can be reacted with the amine or hydroxy groups of the polymer and of the diphosphine at room temperature or elevated temperature, for example from 30° to 100° C. in accordance with methods known in the literature.

The subsequent introduction of, for example, a hydroxy group into highly crosslinked poly-styrene can be carried out in accordance with known procedures. First chloromethylation is carried out as described in J. Mol. Catal. 51 (1989), 13–27 and then hydrolysis in accordance with the method given by J. M. Frechet et al. in Polymer, 20 (1979) 675–680.

The compounds of formula VIIId can be reacted to form ferrocenyldiphosphines fixed on inorganic carriers by means of an analogous reaction procedure—as disclosed in EP-A-0 496 699.

The solid carrier T can be a silicate or a semi-metal oxide or metal oxide or a glass, which are preferably present in the form of powders having average particle diameters of from 10 nm to 2000 μm, preferably from 10 nm to 1000 μm and especially from 10 nm to 500 μm.

They may be either compact or porous particles. Porous particles preferably have large internal surface areas, for example from 1 to 1200 m², preferably from 30 to 600 m². Examples of oxides and silicates are $SiO_2$, $TiO_2$, $ZrO_2$, MgO, NiO, $WO_3$, $Al_2O_3$, $La_2O_3$, silica gels, clays and zeolites. Preferred carriers are silica gels, aluminium oxide, titanium oxide or glass and mixtures thereof. An example of a glass as carrier is "controlled pore glass" which is commercially available.

Using the organically or inorganically fixed diphosphines it is possible to prepare metal complexes of rhodium or iridium by reacting the organic or inorganic carriers to which the diphosphines are bonded with a metal compound of the formula $[Me(Y)D]_2$ or $Me(Y)_2^+E^-$ wherein Me is rhodium or iridium, Y represents two monoolefin ligands or one diene ligand; D is —Cl, —Br or —I and $E^-$ is the anion of an oxy acid or complex acid.

Metal complexes in which Y is 1,5-hexadiene, 1,5cyclooctadiene or norbornadiene are preferred.

In the metal complexes according to the invention D is preferably —Cl, —Br or —I.

In the preferred metal complexes, $E^-$ is $ClO_4^-$, $CF_3SO_3^-$, $CH_3SO_3^-$, $HSO_4^-$, $BF_4^-$, $B(phenyl)_4^-$, $PF_6^-$, $SbCl_6^-$, $AsF_6^-$ or $SbF_6^-$.

The reaction is advantageously carried out under an inert gas atmosphere, for example argon, and expediently at temperatures of from 0 to 40° C., preferably at room temperature, in the case of soluble polymer-bonded diphosphines. A solvent or mixture of solvents is advantageously co-used, for example hydrocarbons (benzene, toluene, xylene), halogenated hydrocarbons (methylene chloride, chloroform, carbon tetrachloride, chlorobenzene), alkanols (methanol, ethanol, ethylene glycol monomethyl ether), and ethers (diethyl ether, dibutyl ether, ethylene glycol dimethyl ether) or mixtures thereof.

Preferably the metal complexes are used for the asymmetric hydrogenation of prochiral compounds having carbon-carbon or carbon-hetero atom double bonds, especially the Ir complexes for the hydrogenation of asymmetric ketimines. Such hydrogenations with soluble homogeneous ferrocenyldiphosphine metal complexes are disclosed, for example, in EP-A-612 758.

The following Examples illustrate the invention.
General process procedure:
All operations are carried out under an inert gas atmosphere (argon or nitrogen).
Abbreviations used:
TMEDA: N,N,N,N-tetramethylethylenediamine
n-BuLi: n-butyllithium
COD: 1,5-cyclooctadiene

EXAMPLE A1

Preparation of the Compound of Formula 1

(R)-N,N-Dimethyl-1-[(S)-1',2bis(chloro)ferrocenyl]ethylamine

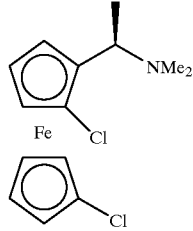

(1)

2.92 ml (4.6 mmol) of a 1.6 M n-BuLi solution are added dropwise at room temperature, with stirring, to a solution of 1 g (3.9 mmol) of (R)-N,N-dimethyl-1-ferrocenylethylamine in 8 ml of diethyl ether. After 1.5 hours, a further solution consisting of 2.92 ml (4.6 mmol) of a 1.6 M BuLi solution in hexane and 0.67 ml (4.4 mmol) of TMEDA is added dropwise and the reaction mixture is stirred for 5 hours. The dark-brown, cloudy reaction mixture is then cooled to −72 to −78° C. with a dry ice/isopropanol bath and, with stirring, 2.21 g (9.4 mmol) of hexachloroethane are slowly added in portions in such a manner that the temperature of the mixture does not exceed −74° C. The mixture is stirred for a further 1 hour with cooling and then for a further 2 hours without cooling. 20 ml of ice-water are added to the resulting orange suspension and the mixture is repeatedly extracted by shaking wth 5 ml of ethyl acetate.

The organic phases are collected, washed with water, dried with Na₂SO₄ and concentrated in a rotary evaporator. The brown crude product is purified by chromatography (silica gel: Merck 60; eluant: acetone). 0.54 g of compound 2 is obtained (yield 43%, orange oil).

Analysis: $^1$H—NMR (CDCl₃): δ 1.53 (d, 3H, J=7, C—CH₃), 2.13 (s, 6H, N(CH₃)₂), 3.83 (q, 1H, J=7, CH—Me), 4.0–4.5 (m, 7H, C₅H₃FeC₅H₄).

Microanalysis, calculated for $C_{14}H_{17}Cl_2FeN$: C, 51.57; H, 5.26; N, 4.30; Cl, 21.75. found: C, 51.42; H, 5.28; N, 4.28; Cl, 21.48.

EXAMPLE A2

Preparation of the Compound of Formula 2

(R)-N,N-Dimethyl-1-[(S)-1',2bis(bromo)ferrocenyl] ethylamine

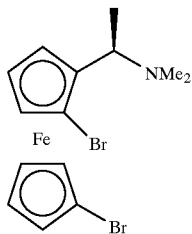

(2)

20.6 ml (33 mmol) of a 1.6 M n-BuLi solution are added dropwise at room temperature, with stirring, to a solution of 7.71 g (30 mmol) of (R)-N,N-dimethyl-1-ferrocenylethylamine in 50 ml of diethyl ether. After 1.5 hours, a further solution consisting of 22.5 ml (36 mmol) of a 1.6 M BuLi solution in hexane and 4.95 ml (33 mmol) of TMEDA is added dropwise and the reaction mixture is stirred overnight. The dark-brown, cloudy reaction mixture is then cooled to −72 to −78° C. in a dry ice/isopropanol bath and, with stirring, 7.9 ml (66 mmol) of 1,2-dibromotetrafluoroethane are slowly added dropwise in such a manner that the temperature of the mixture does not exceed −74° C. The mixture is stirred for a further 1 hour with cooling and then for a further 2 hours without cooling. 50 ml of ice-water are added to the resulting orange suspension and the mixture is repeatedly extracted by shaking wth 25 ml of ethyl acetate. The organic phases are collected, washed with water, dried with Na₂SO₄ and concentrated in a rotary evaporator. The brown crude product is purified by chromatography (silica gel: Merck 60; eluant: acetone). 7.5 g of compound 2 are obtained (yield 60%, brown oil).

Analysis: $^1$H—NMR (CDCl₃): δ 1.53 (d, 3H, J=7, C—CH₃), 2.13 (s, 6H, N(CH₃)₂), 3.78 (q, 1H, J=7, CH—Me), 4.03–4.5 (m, 7H, C₅H₃FeC₅H₄).

Microanalysis calculated for $C_{14}H_{17}NBr_2Fe$: C, 40.52; H, 4.13; N, 3.38; Br, 38.51; Fe, 13.46. found: :C, 40.80; H, 4.10; N, 3.30; Br, 38.18.

EXAMPLE A3

Preparation of the Compound of Formula 3

(R)-N,N-Dimethyl-1-[(S)-1',2bis(iodo)ferrocenyl] ethylamine

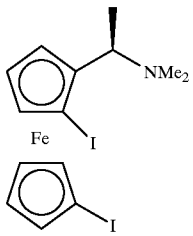

(3)

2.92 ml (4.6 mmol) of a 1.6 M n-BuLi solution are added dropwise at room temperature, with stirring, to a solution of 1 g (3.9 mmol) of (R)-N,N-dimethyl-1-ferrocenylethylamine in 8 ml of diethyl ether. After 1.5 hours, a further solution consisting of 2.92 ml (4.6 mmol) of a 1.6 M BuLi solution in hexane and 0.67 ml (4.4 mmol) of TMEDA is added dropwise and the reaction mixture is stirred for 5 hours. The dark-brown, cloudy reaction mixture is then cooled to −72 to −78° C. in a dry ice/isopropanol bath and, with stirring, 2.37 g (9.3 mmol) of iodine are slowly added in portions in such a manner that the temperature of the mixture does not exceed −74° C. The mixture is stirred for a further 1 hour with cooling and then for a further 2 hours without cooling. 20 ml of ice-water are added to the resulting orange suspension and the mixture is repeatedly extracted by shaking wth 20 ml of ethyl acetate. The organic phases are collected, washed with water, dried with Na₂SO₄ and concentrated in a rotary evaporator. The brown crude product is purified by chromatography (silica gel: Merck 60; eluant: acetone). 0.17 g of compound 3 is obtained (yield 9%, reddish-brown oil).

Analysis: $^1$H—NMR (CDCl₃): δ 1.50 (d, 3H, J=7, C—CH₃), 2.15 (s, 6H, N(CH₃)₂), 3.65 (q, 1H, J=7, CH—Me), 4.03–4.5 (m, 7H, C₅H₃FeC₅H₄).

Microanalysis calculated for $C_{14}H_{17}NI_2Fe$: C, 33.04; H, 3.37; N, 2.75; I, 49.87. found: C, 32.89; H, 3.56; N, 2.63; I, 49.08.

EXAMPLE A4

Preparation of the Compound of Formula 4

(R)-N,N-Dimethyl-1-[1'-(bromo),(S)-2-(diphenylphosphino)ferrocenyl]ethylamine

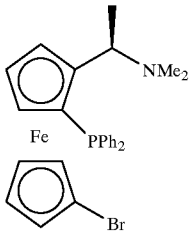

(4)

0.37 ml (0.6 mmol) of a 1.6 M BuLi solution in hexane is added dropwise at −40 to −30° C., with stirring, to a solution of 250 mg (0.6 mmol) of the compound from Example 2 (compound 2) in 4 ml of diethyl ether. The mixture is then cooled to −78° C. and 0.133 ml (0.72 mmol) of Cl—PPh$_2$ is slowly added. The mixture is then allowed to rise slowly to room temperature and is then stirred for a further 1 hour. 10 ml of water are then added to the resulting yellow suspension and the mixture is repeatedly extracted by shaking with ethyl acetate. The organic phases are collected, washed with water, dried with Na$_2$SO$_4$ and concentrated in a rotary evaporator. The yellowish-brown crude product is purified by chromatography over silica gel or Alox. 159 mg of compound 4 are obtained (yield 51%, orangeish-brown almost solid). If the same reaction is carried out in pentane under conditions that are otherwise the same, a yield of 61% is obtained.

Analysis: $^1$H—NMR (CDCl$_3$): δ 1.25 (d, 3H, J=7, C—CH$_3$), 1.75 (s, 6H, N(CH$_3$)$_2$), 4.15 (m, 1 H, J=7, CH—Me), 3.7–4.4 (m, 7H, C$_5$H$_3$FeC$_5$H$_4$), 7.1–7.65 (m, 10H, P(C$_6$H$_5$)$_2$. $^{31}$P—NMR (CDCl$_3$): δ −24.568

EXAMPLE A5

Preparation of the Comoound of Formula 5

(R)-N,N-Dimethyl-1-[1'-(1"-dimethylsilyl-3"-chloropropyl)-(S)-2-diphenylphosphino-ferrocenyl]ethylamine

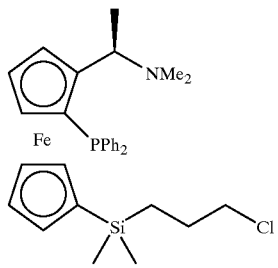

(5)

0.2 ml (0.32 mmol) of a 1.6 M BuLi solution in hexane is added dropwise at −40 to −30° C., with stirring, to a solution of 136 mg (0.26 mmol) of compound 4 from Example 4 in 4 ml of diethyl ether. The mixture is then cooled to −78° C. and 0.056 ml (0.34 mmol) of 3-chloro-propyl-dimethylchlorosilane is slowly added. The mixture is then allowed to rise slowly to room temperature and is then stirred for a further 1 hour. 10 ml of water are then added to the resulting orange suspension and the mixture is repeatedly extracted by shaking with ethyl acetate. The organic phases are collected, washed with water, dried with Na$_2$SO$_4$ and concentrated in a rotary evaporator. The yellowish-brown crude product is purified by chromatography (silica gel: Merck 60; eluant: ethyl acetate). 85 mg of compound 5 are obtained (yield 50%, orange almost solid).

Analysis: $^1$H—NMR (CDCl$_3$): δ 0.05 (s, 3H,Si—CH$_3$), 0.15 (s, 3H,Si—CH$_3$), 0.61 (m, 2H, CH$_2$—Si), 1.28 (d, 3H, J=7, C—CH$_3$), 1.5–1.9 (m, 2H, CH$_2$—CH$_2$—Cl1.75), 1.78 (s, 6H, N(CH$_3$)$_2$), 3.4 (t, 3H, CH$_2$—Cl), 3.5–4.4, (m, 8H, C5H$_4$FeC$_5$H$_3$CH), 7.1–7.65 (m, 10H, P(C$_6$H$_5$)$_2$. $^{31}$P—NMR (CDCl$_3$): δ −23.306

EXAMPLE A6

Preparation of the Compound of Formula 6

(R)-1-[1'-(Bromo)-(S)-2-diphenylphosphino-ferrocenyl]ethyldicyclohexylphosphine

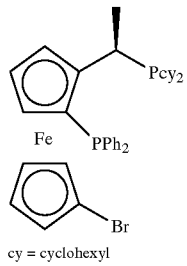

(6)

cy = cyclohexyl

A mixture of 199 mg (0.38 mmol) of compound 4 from Example 4 and 0.093 ml of dicyclo-hexylphosphine in 2 ml of acetic acid is stirred at 100° C. (bath temperature) for 2.5 hours. After cooling, 10 ml of water are added to the orange solution and the mixture is repeatedly extracted by shaking with toluene. The organic phases are collected, washed with water, dried with Na$_2$SO$_4$ and concentrated in a rotary evaporator. The orange crude product is purified by chromatography (silica gel: Merck 60; eluant: hexane/ethyl acetate 4/1). 174 mg of compound 6 are obtained (yield 67%, orange almost solid).

Analysis: $^1$H—NMR (CDCl$_3$): δ 0.9–2 (m, 25H, P(C$_6$H$_{11}$)$_2$, C—CH$_3$), 3.25 (m, 1H, CH—CH$_3$), 3.45–4.4 (m, 7H, C$_5$H$_3$FeC$_5$H$_4$), 7.1–7.7 (m, 10H, P(C$_6$H$_5$)$_2$). $^{31}$P—NMR (CDCl$_3$): δ −27.2 (d, PPh$_2$), 16.0 (d, Pcy$_2$), JPP 35 Hz.

EXAMPLE A7

Preparation of the Compound of Formula 7 a) (R)-1-[1'-(1"-Dimethylsilyl-3"-chloropropyl)-(S)-2-(diphenylphosphino)ferrocenyl]ethyl-dicyclohexylphosphine

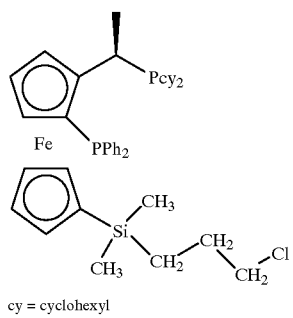

(7)

cy = cyclohexyl 0.36 g (1.8 mmol) of dicyclohexylphosphine in 2 ml of acetic acid is added to 1 g (1.73 mmol) of compound 5 from Example 5 in 4 ml of acetic acid and the mixture is stirred at 95° C. in an oil bath for 90 minutes. After cooling, the reddish-brown solution is extracted by shaking in 10 ml of toluene and 30 ml of a 5% aqueous NaCl solution. The aqueous phase is then extracted by shaking three times with 5 ml of toluene. The organic phases are then collected, washed with 15 ml of water, dried with $Na_2SO_4$ and concentrated in a rotary evaporator under reduced pressure. The crude product is purified by column chromatography (eluant: hexane/diethyl ether). 0.95 g of compound 7 is obtained (brown powder, yield 75%).

Characterisation: $^{31}P$—NMR ($CDCl_3$): δ −26.5 (d, $PPh_2$), 15.8 (d, $Pcy_2$), JPP 34 Hz. $^1H$—NMR ($CDCl_3$): δ 0.05 (s, 3H, Si—$CH_3$), 0.15 (s, 3H, Si—$CH_3$), 0.6 (m, 2H, $CH_2$—Si), 0.9–2.0 (m, 27H, cy, C$\underline{H}_2$—$CH_2$—Cl, CH—C$\underline{H}_3$), 3.41 (t, 2H, J=7, $CH_2$—Cl), 3.1–4.5 (m, 8H, $C_5H_4FeC_5H_3CH$), 7.1–7.75 (m, 10H, $P(C_6H_5)_2$).

b) (R)-1-[1'-(1''-Dimethylsilyl-3''-chloropropyl)-(S)-2-(diphenylphosphino)ferrocenyl]ethyl-dicyclohexylphosphine 0.2 ml (0.32 mmol) of a 1.6 M butyl-Li solution in hexane is added dropwise at −40 to −30° C., with stirring, to a solution of 167 mg (0.25 mmol) of compound 6 from Example 6 in 3 ml of diethyl ether. The mixture is then cooled to −78° C. and 0.057 ml (0.35 mmol) of 3-chloropropyl-dimethylchlorosilane is slowly added. The mixture is then allowed to rise slowly to room temperature and is then stirred for a further 1 hour. 5 ml of water are then added to the resulting orange suspension and the mixture is repeatedly extracted by shaking with $CH_2Cl_2$. The organic phases are collected, washed with water, dried with $Na_2SO_4$ and concentrated in a rotary evaporator. The orange crude product is purified by chromatography (silica gel: Merck 60; eluant: hexane/ethyl acetate 4/1). 127 mg of compound 7 are obtained (yield 70%, orange almost solid).

Characterisation: $^{31}P$—NMR ($CDCl_3$): δ −26.5 (d, $PPh_2$), 15.8 (d, $Pcy_2$), JPP 34 Hz. $^1H$—NMR ($CDCl_3$): δ 0.05 (s, 3H, Si—$CH_3$), 0.15 (s, 3H, Si—$CH_3$), 0.6 (m, 2H, $CH_2$—Si), 0.9–2.0 (m, 27H, cy, C$\underline{H}_2$—$CH_2$—Cl, CH—C$\underline{H}_3$), 3.41 (t, 2H, J=7, $CH_2$—Cl), 3.1–4.5 (m, 8H, $C_5H_4FeC_5H_3CH$), 7.1–7.75 (m, 10H, $P(C_6H_5)_2$).

EXAMPLE A8

Preparation of the Compound of Formula 8
The primary amine (8) is prepared by way of Gabriel synthesis (conversion of the chloride into the phthalimide and freeing of the amine with hydrazine hydrate) from compound (7) Example 7:

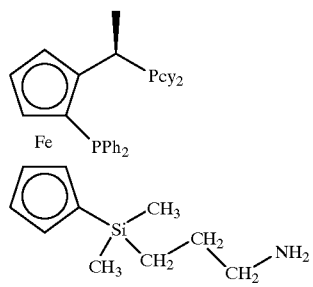

(8)

450 mg of potassium phthalimide and 120 mg of hexadecyltributylphosphonium bromide (catalyst) are added to a solution of 1.4 g (1.94 mmol) of the compound of formula 7 from Example 7 in 3 ml of DMF and the mixture is stirred at 96° C. for 1.5 hours. After cooling, the mixture is extracted by shaking in water/toluene and the organic phase is dried with sodium sulfate and concentrated in a rotary evaporator. After purification by chromatography (eluant: hexane/ethyl acetate), 1.32 g of orange powder are obtained (yield 81%).

Characterisation: $^{31}P$—NMR ($CDCl_3$): δ −26.5 (d, $PPh_2$), 15.8 (d, $Pcy_2$), JPP 34 Hz. $^1H$—NMR ($CDCl_3$): δ characteristic signals 3.58 (t, 2H, J=7, $CH_2$—N), 7.6–7.9 (m, 4H, phthalimide).

1.24 g (1.48 mmol) of the orange powder and 0.3 ml of hydrazine hydrate in 12 ml of ethanol are heated at reflux for 2 hours. After cooling, 25 ml of methylene chloride are added and the suspension is filtered and washed. The solution is concentrated in a rotary evaporator under reduced pressure and the product is purified by chromatography (eluant MeOH with 2% triethylamine). 0.98 g of orange, almost solid oil of the compound of formula 8 is obtained (yield 94%).

Characterisation: $^{31}P$—NMR ($CDCl_3$): δ −26.5 (d, $PPh_2$), 15.7 (d, $Pcy_2$). JPP 33 Hz. $^1H$—NMR ($CDCl_3$): δ characteristic signals 2.6 (t, 2H, J=7, $CH_2$—N).

EXAMPLE A9

Synthesis of the Ligand of Formula 9 Immobilisable on Organic Carriers

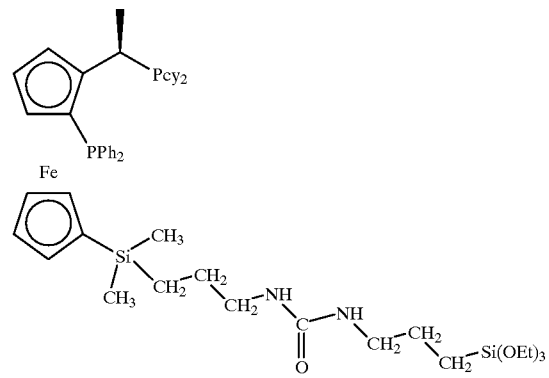

(9)

0.24 ml (0.9 mmol) of 1-triethoxysilyl-3-isocyanatopropane is added dropwise to a solution of 506 mg (0.71 mmol) of the compound of formula 8 from Example 8 in 10 ml of methylene chloride and the mixture is stirred at room temperature overnight. The solvent is then evaporated off in a rotary evaporator under reduced pressure and the crude product is purified by chromatography (eluant: ethyl acetate). 530 mg of an orange, viscous foam of the compound of formula 7c are obtained (yield 72%).

Characterisation: $^{31}P$—NMR ($CDCl_3$): δ −26.5 (d, $PPh_2$), 15.7 (d, $Pcy_2$), JPP 33 Hz. $^1H$—NMR ($CDCl_3$): δ 1.22 (t, J=7, 9H, O—$CH_2$—$CH_3$), 2.95–3.25 (m, 4H, $CH_2$—NH—C(O)—NH—$CH_2$), 3.81 (q, J=7, 6H, O—$CH_2$).

EXAMPLE A10

Preparation of the Compound of Formula 10

Preparation of (R)-N,N-dimethyl-1-[1'-(bromo)-(S)-2-diphenylphosphino-ferrocenyl]ethyl-dixylylphosphine

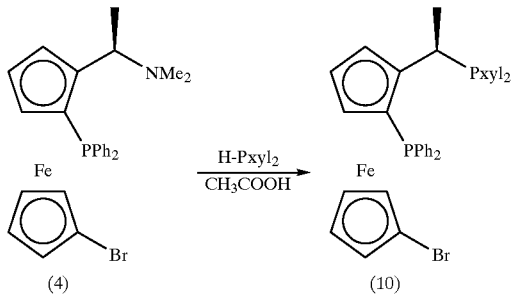

6.75 g (13 mmol) of the compound of formula 4 and 3.2 g of bis(3,5-xylyl)phosphine (13.2 mmol) in 5 ml of toluene are stirred in 80 ml of acetic acid at 100° C. (bath temperature) for 4 hours. After cooling, the reaction mixture is concentrated to dryness in vacuo in a rotary evaporator at 40–50° C. and then purified by chromatography (silica gel: Merck 60; eluant: hexane/ethyl acetate 20/1). 7.7 g of product are obtained (yield 82%, orange powder).

Analysis: $^1$H—NMR (CDCl$_3$): δ 1.45 (t, 3H, C—CH$_3$), 2.20 and 2.28 (each 1 s, 12H, Ph—C$\underline{H}_3$), 3.45–4.3 (m, 7H, C$_5$H$_3$FeC$_5$H$_4$ and 1H, C$\underline{H}$—CH$_3$), 6.75–7.7 (m, 16H, P(C$_6$H$_5$)$_2$ and P(C$_6$$\underline{H}_3$Me$_2$) $^{31}$P—NMR (CDCl$_3$): δ 7.75 (d, Pxylyl$_2$), −26.4 (d, PPh$_2$), JPP 22 Hz.

EXAMPLE A11

Preparation of the Compound of Formula 11

(R)-N,N-Dimethyl-1-[1'-(bromo)-(S)-2-diphenylphosphino-ferrocenyl]ethyldiphenyl-phosphine

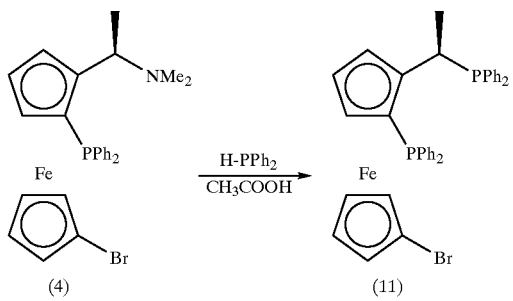

2.03 g (3.9 mmol) of the compound of formula 4 and 0.8 ml of diphenylphosphine (4.5 mmol) are stirred in 20 ml of acetic acid at 100° C. (bath temperature) for 4 hours. After cooling, 50 ml of water are added to the orange solution and the mixture is repeatedly extracted by shaking with toluene. The organic phases are collected, washed with water, dried with Na$_2$SO$_4$ and concentrated in a rotary evaporator. The orange crude product is purified by chromatography (silica gel: Merck 60; eluant: hexane/ethyl acetate 30/1). 2.1 g of product are obtained (yield 81%, orange powder).

Analysis: $^1$H—NMR (CDCl$_3$): δ 1.45 (t, 3H, C—CH$_3$), 3.5–4.3 (m, 7H, C$_5$H$_3$FeC$_5$H$_4$ and 1H, C$\underline{H}$—CH$_3$), 7.1–7.38 (m, 20H, P(C$_6$H$_5$)$_2$) $^{31}$P—NMR (CDCl$_3$): δ 7.12 (d, CH(Me)—PPh$_2$, −27.18 (d, PPh$_2$), JPP 25 Hz.

EXAMPLE A12

Preparation of the Compound of Formula 12

(R)-1-[1'-(1"-Dimethylsilyl-3"-chloropropyl)-(S)-2-(diphenylphosphino)ferrocenyl]ethyldi-3,5-xylylphosphine starting from the compound of formula (10) from Example 10.

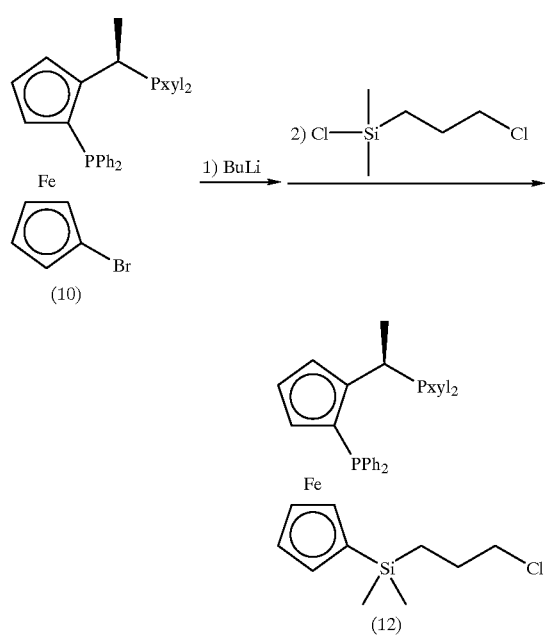

2.5 mmol of a 1.6 M BuLi solution in hexane are added dropwise at −40 to −30° C., with stirring, to a solution of 1 g (1.9 mmol) of the compound of formula (10) in 18 ml of diethyl ether. The mixture is then cooled to −78° C. and 460 mg (2.69 mmol) of 3-chloropropyl-dimethylchlorosilane are slowly added. The mixture is then allowed to rise slowly to room temperature and is then stirred for a further 1 hour. 20 ml of water are then added and the reaction mixture is repeatedly extracted by shaking with CH$_2$Cl$_2$. The organic phases are collected, washed with water, dried with Na$_2$SO$_4$ and concentrated in a rotary evaporator. The orange crude product is purified by chromatography (silica gel: Merck 60; eluant: hexane/diethyl ether 30/1). 1.1 g of the compound of formula (10) are obtained (yield 75%, orange powder).

Characterisation: $^{31}$P—NMR (CDCl$_3$): δ −26.5 (d, PPh$_2$), 6.7 (d, Pxyl$_2$), JPP 21 Hz. $^1$H—NMR (CDCl$_3$): δ 0.04 (s, 3H, Si—CH$_3$), 0.14 (s, 3H, Si—CH$_3$), 0.6 (m, 2H, CH$_2$—Si), 1.43 (d, 3H, CH—C$\underline{H}_3$), 1.5–1.7 (m, 2H, C$\underline{H}_2$—CH$_2$—Cl), 2.20 and 2.30 (two s, each 6H, C$_6$H$_3$(C$\underline{H}_3$)$_2$, 3.41 (t, 2H, J=7, CH$_2$—Cl), 3.2–4.5 (m, 8H, C$_5$H$_4$FeC$_5$H$_3$CH), 6.7–7.8 (m, 16H, P(C$_6$H$_5$)$_2$ and P(C$_6$H$_3$Me$_2$)$_2$).

EXAMPLE A13

Preparation of the Compound of Formula 13

The primary amine of formula 13 is prepared by way of Gabriel synthesis (conversion of the chloride into the phthalimide and freeing of the amine with hydrazine hydrate):

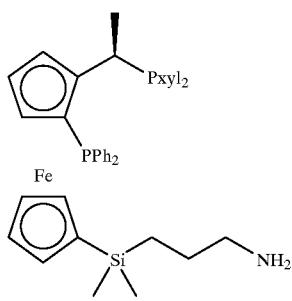

(13)

464 mg of potassium phthalimide (2.5 mmol) and 125 mg of hexadecyltributyl-phosphonium bromide (catalyst) are added to a solution of 1.53 g (2 mmol) of the compound of formula 12 in 4 ml of DMF and the mixture is stirred at 100° C. (bath temperature) for 2 hours. After cooling, the mixture is extracted by shaking in water/toluene and the organic phase is dried with sodium sulfate and concentrated in a rotary evaporator. After purification by chromatography (silica gel: Merck 60; eluant: hexane/ethyl acetate 9/1), 1.58 g of phthalimide are obtained in the form of an orange powder (yield 90%).

Characterisation: $^{31}$P—NMR (CDCl$_3$): δ −25.3 (d, PPh$_2$), 7.0 (d, Pxyl$_2$), JPP 21 Hz. $^1$H—NMR (CDCl$_3$): δ 0.04 (s, 3H, Si—CH$_3$), 0.1 (s, 3H, Si—CH$_3$), 0.5 (m, 2H, CH$_2$—Si),1.44 (m, 3H, CH—CH$_3$), 1.4–1.7 (m, 2H, CH$_2$—CH$_2$—N), 2.20 and 2.27 (two s, each 6H, C$_6$H$_3$(CH$_3$)$_2$), 3.58 (t, 2H, J=7, CH$_2$—N), 3.2–4.4 (m, 8H, C$_5$H$_4$FeC$_5$H$_3$CH), 6.7–7.8 (m, 16H, P(C$_6$H$_5$)$_2$), P(C$_6$H$_3$(Me)$_2$), 7.6–7.9 (m, 4H, phthalimide).

1.58 g (1.78 mmol) of the phthalimide obtained in the first step and 0.5 ml of hydrazine hydrate in 20 ml of ethanol are boiled at reflux for 2 hours. After cooling, 50 ml of toluene are added and the suspension is filtered and washed with 2×10 ml of water. The solution is dried with sodium sulfate and concentrated in a rotary evaporator under reduced pressure; the product is again made into a suspension with 20 ml of diethyl ether and filtered. After concentration in a rotary evaporator, 1.34 g of an orange foam are obtained (yield 99%).

Characterisation: $^{31}$P—NMR (CDCl$_3$): δ −25.2 (d, PPh$_2$), 6.7 (d, Pxyl$_2$), JPP 22 Hz. $^1$H—NMR (CDCl$_3$): δ 0.03 (s, 3H, Si—CH$_3$), 0.11 (s, 3H, Si—CH$_3$), 0.48 (m, 2H, CH$_2$—Si), 1.15–1.45 (m, 2H, CH$_2$—CH$_2$—N), 1.45 (m, 3H, CH—CH$_3$), 2.20 and 2.27 (two s, each 6H, C$_6$H$_3$(CH$_3$)$_2$), 2.58 (t, 2H, J=7, CH$_2$—N), 3.2–4.45 (m, 8H, C$_5$H$_4$FeC$_5$H$_3$CH), 6.7–7.75 (m, 16H, P(C$_6$H$_5$)$_2$), P(C$_6$H$_3$(Me)$_2$).

EXAMPLE A14

Preparation of the Compound of Formula 14

Synthesis of the ligand of formula (14) immobilisable on inorganic carriers

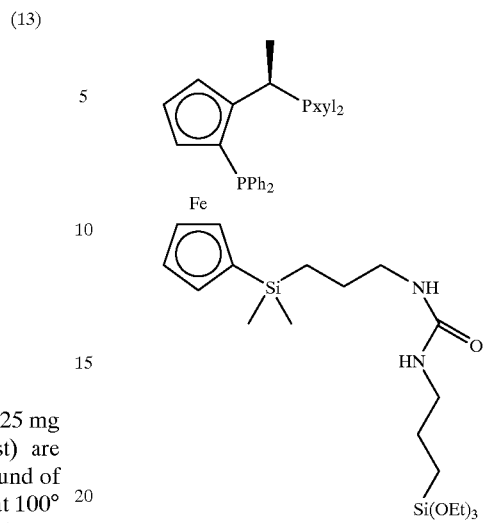

(14)

0.7 ml (2.6 mmol) of 1-triethoxysilyl-3-isocyanatopropane is added dropwise to a solution of 1.5 g (1.99 mmol) of the compound of formula (13) in 10 ml of methylene chloride and the mixture is stirred overnight at room temperature. The solvent is then evaporated off in a rotary evaporator under reduced pressure and the crude product is purified by chromatography (silica gel: Merck 60, eluant: hexane/ethyl acetate). 1.47 g of an orange, viscous foam are obtained (yield 74%).

Characterisation: $^{31}$P—NMR (CDCl$_3$): δ −25.2 (d, PPh$_2$), 6.7 (d, Pxyl$_2$), JPP 21 Hz. $^1$H—NMR (CDCl$_3$) characteristic signals: δ 0.03 (s, 3H, Si—CH$_3$), 0.11 (s, 3H, Si—CH$_3$), 0.48 (m, 2H, CH$_2$—Si-cp), 0.61 (m, 2H, CH$_2$—Si(OEt)$_3$), 1.2–1.8 (m, 4H, CH$_2$CH$_2$NHCONHCH$_2$CH$_2$), 1.22 (t, J=7, 9H, O—CH$_2$—CH$_3$), 1.47 (m, 3H, CH—CH$_3$), 2.20 and 2.28 (two s, each 6H, C$_6$H$_3$(CH$_3$)$_2$), 2.95–3.25 (m, 4H, CH$_2$—NHCONH—CH$_2$), 3.83 (q, J=7, 6H, O—CH$_2$), 6.7–7.8 (m, 16H, P(C$_6$H$_5$)$_2$), P(C$_6$H$_3$(Me)$_2$). Mass spectrum: 1001 (M+H$^+$).

EXAMPLE B

Ligands Immobilised on Silica Gel or Polystyrene

Examples B1–B3 Ligands immobilised on silica gel.

Immobilisation: Before use the carrier is dried at 130° C. for 3 hours under a high vacuum and then placed under argon. Then a solution of immobilisable ligand of formula 9 from Example A9 or of formula 14 from Example A14 in toluene is added and the mixture is stirred at 85–90° C. for 20 hours. After cooling and settling, the supernatant solution is drawn off using a syringe. The mixture is then washed six times with MeOH (7 ml per g of carrier each time) and finally dried at 40–50° C. under a high vacuum. The results are given in Table 1.

TABLE 1

| No. | Immobilis-able ligand No. | Amount [mg] | Carrier type | Amount [g] | Amount toluene [ml] | Analysis P content [%] | Loading mmol ligand per g carrier |
|---|---|---|---|---|---|---|---|
| B1 | 9 | 238 | Grace 332 | 2.2 | 9.8 | 0.1 | 0.098 |
| B2 | 9 | 100 | Grace 332 | 2.2 | 9.8 | 0.26 | 0.041 |
| B3 | 14 | 300 | Grace 332 | 3.0 | 24.0 | 0.33 | 0.052 |

The carrier used is supplied by the W. R. Grace company: Grace 332: spec. surface=320 m$^2$/g, particle size=35–70 micrometers.

Example B4 Ligands immobilised on polystyrene

In a vessel having a stirrer and a glass frit, 900 mg of polymer (aminomethylated poly-styrene, crosslinked with 1% divinyl benzene, amine content=0.56 mmol/g, supplied by: Novabiochem, 01-64-0010), which has been dried under a high vacuum at 50° C., are stirred in 32 ml of methylene chloride until the carrier has swelled. Then 1.2 ml (8.3 mmol) of 2,4-toluylene diisocyanate (TDI) are rapidly added and the mixture is stirred for a further 1 hour. The excess TDI is then removed by filtering off the solution and washing five times with 30 ml of methylene chloride. The carrier that has reacted with the TDI is then stirred in 30 ml of methylene chloride, and a solution of 100 mg (0.133 mmol) of the compound of formula (13) from Example A13 in 2 ml of methylene chloride is added dropwise thereto. The mixture is stirred overnight. In order to convert residual isocyanate groups into carbamates; 10 ml of ethyl alcohol containing 30 μl of triethylamine are added as catalyst and the mixture is stirred overnight at 40° C. The yellowish-orange carrier is then filtered off and washed five times using 20 ml of methylene chloride each time. Finally the carrier is dried under a high vacuum.

Analysis: P content=0.62%. This corresponds to a loading of 0.1 mmol of ligand per g of carrier.

EXAMPLE C1

Hydrogenations

General: All operations are cared out under inert gas. The 50 ml steel autoclave is equipped with a magnetic stirrer (1500 rev/min) and a flow interrupter. Prior to each hydrogenation the inert gas in the autoclave is displaced by hydrogen in 4 cycles (10 bar, normal pressure). Then the desired hydrogen pressure is established in the autoclave and the hydrogenation is started by switching on the stirrer. The conversion is determined by gas chromatography and the optical yield is determined by means of HPLC (column: Chiracel OD), there being used for that purpose a sample that has been purified by flash chromatography (silica gel: Merck 60, eluant=hexane/ethyl acetate).

EXAMPLE C1

A solution of 4.06 mg of [Rh(COD)$_2$]BF$_4$ in 3.3 ml of methanol is added to 122 mg of ligand from Example B1 (ligand 9) and the mixture is stirred slowly, the yellow solution being completely decolourised. Then 554 mg of substrate (N-(2',6'-dimethylphen-1'-yl)-N-(methoxyacetyl)-1-methoxycarbonyl-ethenylamine) dissolved in 5 ml of methanol are added and the mixture is heated to 40° C. in an oil bath and hydrogenated that temperature. After 1 hour, the reaction is discontinued and the hydrogen in the hydrogenation flask is replaced by inert gas. The catalyst is allowed to settle and the supernatant solution is drawn off using a syringe. The conversion is complete and the optical yield is 82.2% (R).

EXAMPLE C2

A solution of 3.5 mg of [Ir(COD)Cl]$_2$ (0.0104 mmol Ir) in 2 ml of THF is added all at once to 250 mg (0.013 mmol) of ligand from Example B3 fixed to silica gel and the mixture is stirred slowly, the yellow solution being completely decolourised. The catalyst is then allowed to settle and the supernatant THF is drawn off using a syringe and the catalyst is dried under a high vacuum. 10 mg of tetrabutylammonium iodide and finally 4.25 g (20.8 mmol) of imine are added to a second flask, the solution is placed under inert gas and added to the catalyst. The reaction mixture is then introduced under pressure into a 50 ml steel autoclave using a steel capillary against a current of inert gas and then hydrogenated at 25° C. at a hydrogen pressure of 80 bar. After 2 hours the hydrogen is depressurised and the catalyst is filtered off under argon. The conversion is complete and the optical yield is 77.5% (S).

Re-use:

4.25 g (20.38 mmol) of imine and 10 mg of tetrabutylammonium iodide are added all at once to the separated catalyst. The reaction mixture is then introduced under pressure into a 50 ml steel autoclave using a steel capillary against a current of inert gas and then hydrogenated at 25° C. at a hydrogen pressure of 80 bar. After 2 hours, the hydrogen is depressurised and the catalyst is filtered off under argon. The conversion is complete and the optical yield is 77.8% (S).

EXAMPLE C3

60 mg (0.006 mmol) of polymer-bonded Xyliphos from Example B4 are added all at once and stirred in 2 ml of THF for 5 minutes. Then a solution of 1.7 mg of [Ir(COD)Cl]$_2$ (0.005 mmol Ir) in 2 ml THF is added and the mixture is stirred slowly, the yellow solution being decolorised. 5 mg of tetrabutylammonium iodide and 2.1 g (10.2 mmol) of N-(2'-methyl-6'-ethyl-phen-1'-yl)-N-(1-methoxymethyl)-ethylimine are added to a second flask, the solution is placed under inert gas and added to the catalyst. The reaction mixture is then introduced under pressure into a 50 ml steel autoclave using a steel capillary against a current of inert gas and then hydrogenated at 25° C. at a hydrogen pressure of 80 bar. After 16 hours the hydrogenation is discontinued, the hydrogen is depressurised and the catalyst is filtered off. The conversion is 68% after that time and the optical yield is 71.1%(S).

What is claimed is:

1. A compound of formula III

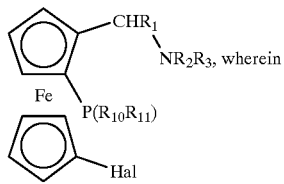

(III)

$R_1$ is $C_1$–$C_8$ alkyl, phenyl or phenyl substituted by from 1 to 3 $C_1$–$C_4$ alkyl or $C_1$–$C_4$ alkoxy substituents;

$R^2$ and $R^3$ are each independently of the other hydrogen or $C_1$–$C_{12}$ alkyl; and Hal is F, Cl, Br or I;

$R_{10}$ and $R_{11}$ are identical or different and are $C_1$–$C_{12}$alkyl, $C_5$–$C_{12}$cycloalkyl, phenyl, $C_5$–$C_{12}$cycloalkyl substituted by $C_1$–$C_4$alkyl or by $C_1$–$C_4$alkoxy, or phenyl substituted by from one to three $C_1$–$C_4$alkyl, $C_1$–$C_4$alkoxy, —$SiR_4R_5R_6$, halogen, —$SO_3M$, —$CO_2M$, —$PO_3M$, —$NR_7R_8$, —$(^+NR_7R_8R_9)X^-$ or $C_1$–$C_5$fluoroalkyl substituents; or the group —$PR_{10}R_{11}$ is a radical of formula IV, IVa, IVb, or IVc

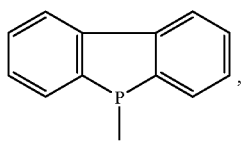

(IV)

(IVa)

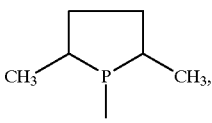

(IVb)

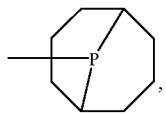

(IVc)

$R_4$, $R_5$ and $R_6$ are each independently of the others $C_1$–$C_{12}$alkyl or phenyl;

$R_7$ and $R_8$ are H, $C_1$–$C_{12}$alkyl or phenyl or $R_7$ and $R_8$ together are tetramethylene, pentamethylene or 3-oxa-1,5-pentylene;

$R_9$ is H or $C_1$–$C_4$alkyl;

M is H or an alkali metal;

$X^-$ is the anion of a monobasic acid.

2. A compound of formula III according to claim 1, wherein $R_{10}$ and $R_{11}$ as alkyl are $C_1$–$C_8$alkyl.

3. A compound of formula III according to claim 1, wherein $R_{10}$ and $R_{11}$ as cycloalkyl contain from 5 to 8 carbon atoms.

4. A compound of formula III according to claim 1, wherein $R_{10}$ and $R_{11}$ are unsubstituted phenyl or phenyl substituted by 1 or 2 substituents.

5. A compound of formula III according to claim 1, wherein $R_{10}$ and $R_{11}$ as substituted phenyl are 2-methyl-, 3-methyl-, 4-methyl-, 2- or 4-ethyl-, 2- or 4-isopropyl-, 2- or 4-tert-butyl-, 2-methoxy-, 3-methoxy-, 4-methoxy-, 2- or 4-ethoxy-, 4-trimethylsilyl-, 2- or 4-fluoro, 2,4-difluoro-, 2- or 4-chloro-, 2,4-dichloro-, 2,4-dimethyl-, 3,5-dimethyl-, 2-methoxy-4-methyl-, 3,5-dimethyl-4-methoxy-, 3,5-dimethyl-4-(dimethylamino)-, 2- or 4-amino-, 2- or 4-methylamino-, 2- or 4-(dimethylamino)-, 2- or 4-$SO_3H$—, 2- or 4-$SO_3Na$—, 2- or 4-[$^+NH_3Cl^-$]—, 3,4,5-trimethylphen-1-yl, 2,4,6-trimethylphen-1-yl, 4-trifluoromethyl-phenyl or 3,5-di(trifluoro-methyl)phenyl.

6. A compound of formula III according to claim 1, wherein $R_{10}$ and $R_{11}$ are cyclohexyl, tert-butyl, phenyl, 2- or 4-methylphen-1-yl, 2- or 4-methoxyphen-1-yl, 2- or 4-(dimethyl-amino)phen-1-yl, 3,5-dimethyl-4-(dimethylamino)phen-1-yl or 3,5-dimethyl-4-methoxyphen-1-yl.

7. A compound of formula VI according to claim 1, wherein $R_{12}$ and $R_{13}$ are $C_1$–$C_8$alkyl.

8. A compound of formula VI according to claim 1, wherein $R_{12}$ and $R_{13}$ are identical and are isopropyl or tert-butyl.

9. A compound of formula VI according to claim 1, wherein $R_{12}$ and $R_{13}$ as cycloalkyl contain from 5 to 8 carbon atoms.

10. A compound of formula VI according to claim 1, wherein $R_{12}$ and $R_{13}$ are unsubstituted phenyl or phenyl substituted by 1 or 2 substituents.

11. A compound of formula VI according to claim 1, wherein $R_{12}$ and $R_{13}$ as substituted phenyl are 2-methyl-, 3-methyl-, 4-methyl-, 2- or 4-ethyl-, 2- or 4-isopropyl-, 2- or 4-tert-butyl-, 2-methoxy-, 3-methoxy-, 4-methoxy-, 2- or 4-ethoxy-, 4-trimethylsilyl-, 2- or 4-fluoro-, 2,4-difluoro-, 2- or 4-chloro-, 2,4-dichloro-, 2,4-dimethyl-, 3,5-dimethyl-, 2-methoxy-4-methyl-, 3,5-dimethyl-4-methoxy-, 3,5-dimethyl-4-(dimethylamino)-, 2- or 4-amino-, 2- or 4-methylamino-, 2- or 4-(dimethylamino)-, 2- or 4-$SO_3H$—, 2- or 4-$SO_3Na$—, 2- or 4-[$^+NH_3Cl^-$]—, 3,4,5-trimethylphen-1-yl, 2,4,6-trimethylphen-1-yl, 4-trifluoromethyl-phenyl or 3,5-di(trifluoro-methyl)phenyl.

12. A compound of formula VI according to claim 1, wherein $R_{12}$ and $R_{13}$ are identical and are phenyl, cyclohexyl, 2- or 4-methylphen-1-yl, 2- or 4-methoxyphen-1-yl, 2- or 4-(dimethyl-amino)phen-1-yl, 3,5-dimethyl-4-(dimethylamino)phen-1-yl or 3,5dimethyl-4-methoxyphen-1-yl.

13. A compound of formula VI according to claim 1, wherein $R_{12}$ and $R_{13}$ are identical radicals and are cyclohexyl or phenyl.

14. A compound of formula I according to claim 1, wherein $R_1$ is methyl and $R_{12}$ and $R_{13}$ are each cyclohexyl or phenyl and $R_{10}$ and $R_{11}$ are phenyl, cyclohexyl or tert-butyl.

15. A process for the preparation of a compound of formula VI, wherein a compound of formula III according to claim 1 reacted with a compound of formula H—P($R_{12}R_{13}$) in acetic acid, with $R_{12}$ and $R_{13}$ being as defined in claim 1.

16. A compound of formula VI

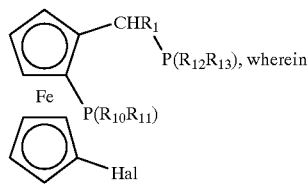

(VI)

$R_1$ is $C_1$–$C_8$ alkyl, phenyl or phenyl substituted by from 1 to 3 $C_1$–$C_4$ alkoxy substituents;

$R_{10}$ and $R_{11}$ are identical or different and are $C_1$–$C_{12}$ alkyl, $C_5$–$C_{12}$ cycloalkyl, phenyl, $C_5$–$C_{12}$ cycloalkyl substituted by $C_1$–$C_4$ alkyl or by $C_1$–$C_4$ alkoxy, or phenyl substituted by from one to three $C_1$–$C_4$ alkyl, $C_1$–$C_4$ alkoxy, —$SiR_4R_5R_6$, halogen, —$SO_3M$, —$CO_2M$, —$PO_3M$, —$NR_7R_8$, —($^+NR_7R_8R_9$)$X^-$ or $C_1$–$C_5$ fluoroalkyl substituents;

Hal is F, Cl, Br or I; and $R_{12}$ and $R_{13}$ are each independently of the other $C_1$–$C_{12}$ alkyl, $C_5$–$C_{12}$ cycloalkyl, phenyl, $C_5$–$C_{12}$ cycloalkyl substituted by $C_1$–$C_4$ alkyl or by $C_1$–$C_4$ alkoxy, or phenyl mono- or poly-substituted by from one to three $C_1$–$C_4$ alkyl, $C_1$–$C_4$ alkoxy, —$SiR_4R_5R_6$, halogen, —$SO_3M$, —$CO_2M$, —$PO_3M$, —$NR_7R_8$, —($^+NR_7R_8R_9$)$X^-$ or $C_1$–$C_5$ fluoroalkyl substituents; or the group —$PR_{12}R_{13}$ is a radical of formula IV, IVa, IVb or IVc

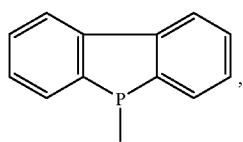

(IV)

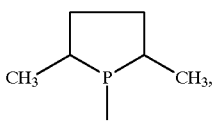

(IVa)

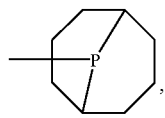

(IVb)

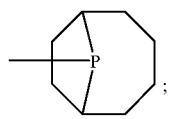

(IVc)

$R_4$, $R_5$ and $R_6$ are each independently of the others $C_1$–$C_{12}$ alkyl or phenyl;

$R_7$ and $R_8$ are H, $C_1$–$C_{12}$ alkyl or phenyl or $R_7$ and $R_8$ together are tetramethylene, pentamethylene or 3-oxa-1,5-pentylene;

$R_9$ is H or $C_1$–$C_4$ alkyl;

M is H or an alkali metal;

$X^-$ is the anion of a monobasic acid.

17. A process for the catalytic hydrogenation of carbon/carbon or carbon/hetero atom double bonds wherein the process comprises contacting a compound containing the double bonds over a rhodium or iridium ligand of formula III.

18. A process for the catalytic hydrogenation of carbon/carbon or carbon/hetero atom double bonds wherein the process comprises contacting a compound containing the double bonds over a rhodium or iridium ligand of formula VI.

19. An inorganically or polymerically bonded rhodium or iridium ligand of formula VI.

* * * * *

UNITED STATES PATENT AND TRADEMARK OFFICE
CERTIFICATE OF CORRECTION

PATENT NO. : 6,015,919
DATED : January 18, 2000
INVENTOR(S) : Benoit Pugin

It is certified that error appears in the above-identified patent and that said Letters Patent is hereby corrected as shown below:

Column 26, claim 5, line 5, "4-fluoro" should read -- 4-fluoro- --.
Column 26, claim 7, line 1, "claim 1" should read -- claim 16 --.
Column 26, claim 8, line 1, "claim 1" should read -- claim 16 --.
Column 26, claim 9, line 1, "claim 1" should read -- claim 16 --.
Column 26, claim 10, line 1, "claim 1" should read -- claim 16 --.
Column 26, claim 11, line 1, "claim 1" should read -- claim 16 --.
Column 26, claim 12, line 1, "claim 1" should read -- claim 16 --.
Column 26, claim 13, line 1, "claim 1" should read -- claim 16 --.
Column 26, claim 14, line 1, "claim 1" should read -- claim 16 --.
Column 27, claim 15, line 3, after "claim 1" insert -- is --.
Column 27, claim 15, line 4, "claim 1" should read -- claim 16 --.

Signed and Sealed this

Twentieth Day of February, 2001

Attest:

NICHOLAS P. GODICI

Attesting Officer

Acting Director of the United States Patent and Trademark Office